United States Patent [19]

Murad et al.

[11] Patent Number: 6,005,009

[45] Date of Patent: *Dec. 21, 1999

[54] METHOD OF INHIBITING FIBROSIS WITH PYRIDOXAL BENZOYL HYDRAZONE AND ANALOGS THEREOF

[75] Inventors: Saood Murad; Sheldon R. Pinnell, both of Durham; Huanshu Yang, Carrboro, all of N.C.

[73] Assignee: Duke University, Durham, N.C.

[ * ] Notice: This patent issued on a continued prosecution application filed under 37 CFR 1.53(d), and is subject to the twenty year patent term provisions of 35 U.S.C. 154(a)(2).

[21] Appl. No.: 08/821,063

[22] Filed: Mar. 20, 1997

[51] Int. Cl.⁶ .......................... A61K 31/44; A61K 31/165
[52] U.S. Cl. .......................... 514/615; 514/345; 514/348; 514/349; 514/351; 514/352; 514/357
[58] Field of Search ..................................... 514/332, 335, 514/345, 348, 349, 351, 352, 357, 615

[56] References Cited

FOREIGN PATENT DOCUMENTS 48-007108   2/1973   Japan .

OTHER PUBLICATIONS

Khaidarly, I.N., Probl. Tuberk., 48(3), 82–6 (abstract), 1970.

*Primary Examiner*—Phyllis G. Spivack
*Attorney, Agent, or Firm*—Myers Bigel Sibley & Sajovec

[57] ABSTRACT

Methods of inhibiting fibrosis comprising administering certain pyridoxal benzoyl hydrazones or analogs thereof are disclosed. Preferred hydrazones are pyridoxal benzoyl hydrazone, 3-hydroxyisonicotinaldehyde benzoyl hydrazone and salicylaldehyde benzoyl hydrazone. The methods are useful in treating fibrosing disorders, including dermal fibrosing disorders, fibrosis of internal organs and fibrotic conditions of the eye.

9 Claims, 3 Drawing Sheets

METHOD OF INHIBITING FIBROSIS WITH PYRIDOXAL BENZOYL HYDRAZONE AND ANALOGS THEREOF

This invention was made with Government support under Grant Nos. R01-AR28304 and R37-AR17128 from the National Institutes of Health. The Government has certain rights to this invention.

FIELD OF THE INVENTION

The present invention relates to methods and compositions for inhibiting fibrosis and combating fibrosing disorders in subjects in need of such treatment.

BACKGROUND OF THE INVENTION

Fibrosis, characterized by an excessive accumulation of collagen in the extracellular matrix of the involved organi, is a long-standing and challenging clinical problem for which no effective treatment is currently available. The production of collagen is a finely regulated process, and its disturbance may lead to the development of tissue fibrosis. The formation of fibrous tissue is part of the normal beneficial process of healing after injury. However, in some circumstances there is an abnormal accumulation of fibrous material such that it interferes with the normal function of the affected tissue.

Central to the development of fibrotic conditions, whether spontaneous or induced, is the proliferation of fibroblasts, the major cell type responsible for collagen synthesis. Many common debilitating diseases, such as liver cirrhosis and pulmonary fibrosis, involve the proliferation of fibrous tissue, as do certain skin diseases such as scleroderma, keloids, and hypertrophic scars.

Attempts to control the abnormal accumulation of collagen during fibrosis have focused on several inhibitors of the translational and post-translational reactions in collagen biosynthesis, but their therapeutic value is limited by certain undesirable features, i.e., poor permeability across cell membrane, nonspecificity in action, or toxicity. There is accordingly, a continuing need for new antifibrotic agents.

SUMMARY OF THE INVENTION

A first aspect of the present invention is a method of inhibiting fibrosis in a subject afflicted with a fibrosing disorder. The method comprises administering to the subject an effective amount of a compound of Formula (I):

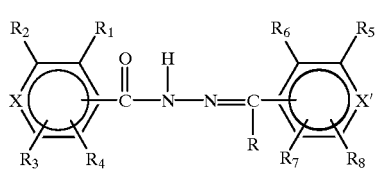

(I)

wherein:
X and X' are each independently selected from the group consisting of N and $CR_9$;
R is selected from the group consisting of H and loweralkyl (preferably H);
$R_1$, $R_2$, $R_3$, $R_4$, $R_5$, $R_6$, $R_7$, and $R_8$ are each independently selected from the group consisting of H, loweralkyl, hydroxy, loweralkylhydroxy, amino, and nitro (preferably H, loweralkyl, hydroxy, or loweralkylhydroxy);

$R_9$ is H or loweralkyl (preferably H);
or a pharmaceutically acceptable salt thereof.

A second aspect of the present invention is a pharmaceutical formulation comprising a compound according to Formula I above, or a pharmaceutically acceptable salt thereof, in an effective fibrosis-combating amount, in a pharmaceutically acceptable carrier.

A third aspect of the present invention is the use of a compound of Formula (I) above, or a pharmaceutically acceptable salt thereof, for the manufacture of a medicament for inhibiting fibrosis in a subject afflicted with a fibrosing disorder.

Our prior patents, U.S. Pat. No. 5,571,846 and U.S. Pat. No. 5,374,660, describe the treatment of fibrosing disorders with benzoic acid hydrazides, but the use of benzoic acid hydrazones is neither suggested nor disclosed.

DETAILED DESCRIPTION OF THE INVENTION

Figure 1:
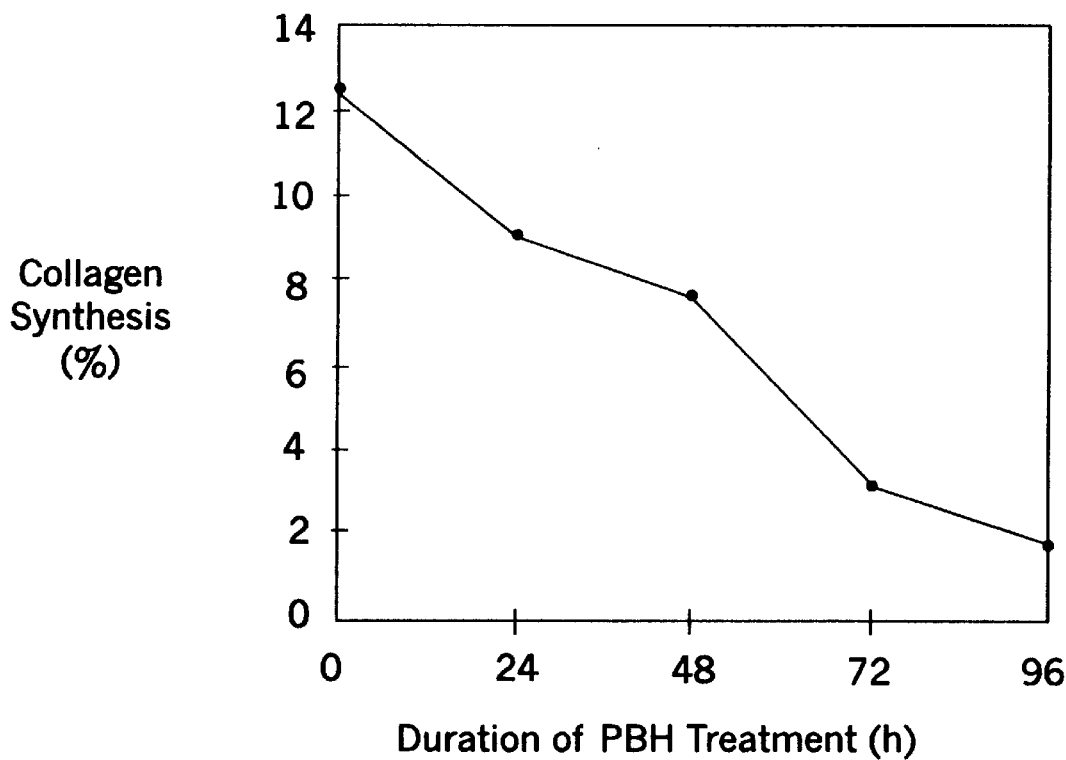
FIG. 1 illustrates collagen synthesis in fibroblast cultures treated for various lengths of time with 50 uM of pyridoxal benzoyl hydrazone.

Compounds of Formula (I) above can be made in accordance with known techniques, and variations thereof that will be apparent to those skilled in the art. See, e.g., M. Vitolo et al., Release of Iron from Ferritin by Pyridoxal Isonicotinoyl Hydrazone and Related Compounds, *Journal of Inorganic Chemistry* 20, 255–262 (1984); D. Johnson et al., An in Vivo Evaluation of Iron-Chelating Drugs Derived from Pyridoxal and its Analogs, *J. Pharmacol. Exp. Ther.* 221, 399–403 (1982).

Specific examples of compounds of Formula (I) above include:
pyridoxal benzoyl hydrazone (PBH),
pyridoxal isonicotinoyl hydrazone (PIH),
pyridoxal phenylacetyl hydrazone (PPH),
3-hydroxyisonicotinaldehyde benzoyl hydrazone (HBH),
salicylaldehyde benzoyl hydrazone (SBH);
3-hydroxyisonicotinaldehyde isonicotinoyl hydrazone; and
salicylaldehyde isonicotinoyl hydrazone.

Compounds of Formula (I) can be produced by commercial sources such as CYCLO₃PSS BIOCHEMICAL CORPORATION, 3646 West 2100 South, Salt Lake City, Utah 84120 (phone 801-972-9499; fax 801-972-3909).

The term "loweralkyl" as used herein refers to C1–C4 alkyl, for example, methyl, ethyl, propyl, and butyl.

Subjects to be treated by the method of the present invention include, but are not limited to, subjects afflicted with a dermal fibrosing disorder, subjects afflicted with fibrosis of an internal organ, and subjects afflicted with fibrotic conditions of the eye.

Dermal fibrosing disorders include, but are not limited to, scleroderma, morphea, keloids, hypertrophic scars, familial cutaneous collagenoma, and connective tissue nevi of the collagen type. Such disorders are preferably treated by administering the compound of Formula (I) topically.

Fibrosis of internal organs (e.g., liver, lung, kidney, heart blood vessels, gastrointestinal tract), occurs in disorders such as pulmonary fibrosis, liver cirrhosis, and scar formation. Such disorders are preferably treated by administering the compound of Formula (I) parenterally or orally.

Fibrotic conditions of the eye include conditions such as diabetic retinopathy, postsurgical scarring (for example, after glaucoma filtering surgery and after cross-eye surgery), and proliferative vitreoretinopathy, which may be treated by the topical application to the eye of an ophthalmic formulation containing a compound of Formula (I).

Subjects to be treated by the method of the present invention include both human and animal (e.g., dog, cat, cow, horse) subjects.

The compound of Formula (I) may be administered in a total amount per day of not more than about 50 mg/kg body weight, more preferably not more than about 25 mg/kg, and most preferably not more than about 10 mg/kg. With respect to minimum dose, the compound of Formula (I) is preferably administered in a total amount per day of at least about 0.01 mg/kg, more preferably at least about 0.1 mg/kg, and most preferably at least about 1 mg/kg. The compound may be administered once or several times a day. When prepared as a formulation for topical administration, the formulation may contain from about 0.1 percent to about 10 percent by weight of the active ingredient.

As noted above, the compounds of Formula (I) may be administered per se or in the form of a pharmaceutically acceptable salt. Such pharmaceutically acceptable salts include, but are not limited to, those prepared from the following acids: hydrochloric, hydrobromic, sulphuric, nitric, phosphoric, maleic, acetic, salicylic, p-toluenesulfonic, tartaric, citric, methanesulphonic, formic, malonic, succinic, naphthalene-2-sulphonic and benzenesulphonic. Also, pharmaceutically acceptable salts can be prepared as alkaline metal or alkaline earth metals, such as sodium, potassium or calcium salts.

The present invention also provides pharmaceutical formulations, both for veterinary and for human medical use, which comprise the compound of Formula (I) together with one or more pharmaceutically acceptable carriers thereof (and optionally any other therapeutic ingredients). The carrier(s) must be pharmaceutically acceptable in the sense of being compatible with the other ingredients of the formulation and not unduly deleterious to the recipient thereof.

The formulations of the present invention include those suitable for topical, ophthalmic, parenteral (including subcutaneous, intramuscular and intravenous), oral, nasal, and rectal administration. Formulations suitable for topical and parenteral administration are preferred.

The formulations may conveniently be presented in unit dosage form and may be prepared by any of the methods well known in the art of pharmacy. All methods include the step of bringing the active compound into association with a carrier, which carrier constitutes one or more accessory ingredients. In general, the formulations are prepared by uniformly and intimately bringing the active compound into association with a liquid carrier, a finely divided solid carrier, or both, and then, if necessary, shaping the product into desired formulations.

Topical formulations comprise the active compound dissolved or suspended in one or more media such as mineral oil, petroleum, polyhydroxy alcohols or other bases used for topical pharmaceutical formulations. The addition of other accessory ingredients may also be desirable.

Formulations suitable for parenteral administration conveniently comprise a sterile aqueous preparation of the active compound, such as sterile pyrogen-free water or saline solution, which is preferably isotonic with the blood of the recipient subject.

Ophthalmic formulations comprise purified aqueous solutions of the compound of Formula (I) with preservative agents and isotonic agents. The formulations are preferably adjusted so that the pH and isotonic factors match that of the eye.

Formulations of the present invention suitable for oral administration may be presented as discrete units such as capsules, cachets, tablets or lozenges, each containing a predetermined amount of the compound of Formula (I) as a powder or granules; or a suspension in an aqueous liquor or non-aqueous liquid such as a syrup, an elixir, an emulsion or a draught.

A tablet may be made by compression or molding, optionally with one or more accessory ingredients. Compressed tablets may be prepared by compressing in a suitable machine, with the active compound being in a free-flowing form such as a powder or granules which is optionally mixed with a binder, disintegrant, lubricant, inert diluent, surface active agent or dispersing agent. Molded tablets comprised of a mixture of the powdered active compound with a suitable carrier may be made by molding in a suitable machine.

A syrup may be made by adding the active compound to a concentrated aqueous solution of a sugar, for example sucrose, to which may also be added any accessory ingredient (s). Such accessory ingredient (s) may include flavorings, suitable preservatives, an agent to retard crystallization of the sugar, and an agent to increase the solubility of any other ingredient, such as a polyhydric alcohol, for example glycerol or sorbitol.

Nasal spray formulations comprise purified aqueous solutions of the active compound with preservative agents and isotonic agents. Such formulations are preferably adjusted to a pH and isotonic state compatible with the nasal mucous membranes.

Formulations for rectal administration may be presented as a suppository with a suitable carrier such as cocoa butter, or hydrogenated fats or hydrogenated fatty carboxylic acids.

In addition to the aforementioned ingredients, the formulations of this invention may further include one or more accessory ingredient(s) selected from diluents, buffers, flavoring agents, binders, disintegrants, surface active agents, thickeners, lubricants, preservatives (including antioxidants) and the like.

The present invention is explained in greater detail in the following non-limiting examples.

EXAMPLE 1

Time Course of Collagen Suppressing Effect of Pyridoxal Benzoyl Hydrazone

FIG. 1 illustrates collagen synthesis in fibroblast cultures treated for various lengths of time with 50 uM of pyridoxal benzoyl hydrazone, as measured by collagenase digestion of proteins labeled with [2,3-$^3$H] proline.

EXAMPLE 2

Figure 2:
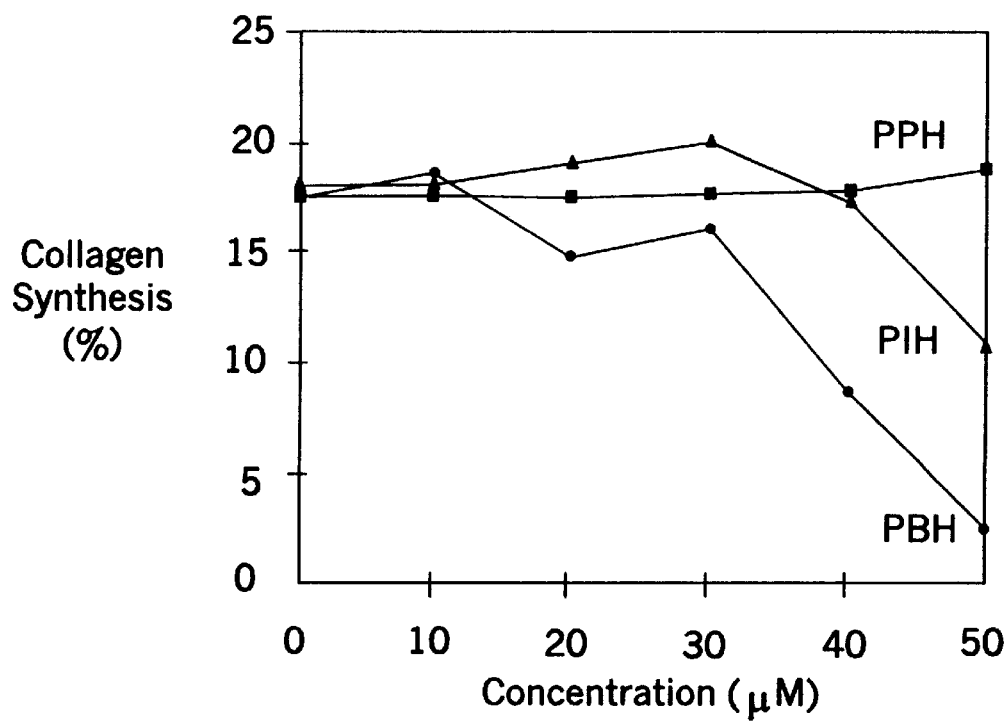
FIG. 2 illustrates collagen synthesis in fibroblast cultures treated for 72 hours with various concentrations of pyridoxal benzoyl hydrazone (PBH), pyridoxal isonicotinoyl hydrazone (PIH), or pyridoxal phenylacetyl hydrazone (PPH).

Concentration Dependence of Collagen Suppressing Effects of Pyridoxal Benzoyl Hydrazone and Acyl Analogs Thereof FIG. 2 illustrates collagen synthesis in fibroblast cultures treated for 72 hours with various concentrations of pyridoxal benzoyl hydrazone (PBH), pyridoxal isonicotinoyl hydrazone (PIH), or pyridoxal phenylacetyl hydrazone (PPH), as measured by collagenase digestion of proteins labeled with [2,3-$^3$H] proline.

EXAMPLE 3

Figure 3:
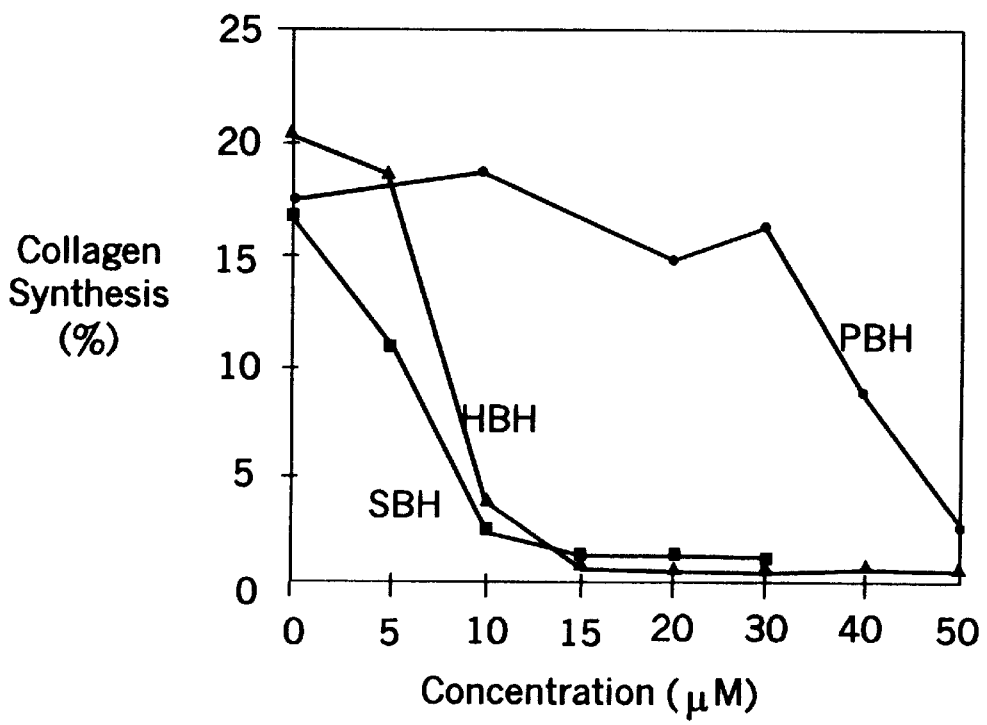
FIG. 3 illustrates collagen synthesis in fibroblast cultures treated for 72 hours with various concentrations of PBH, 3-hydroxyisonicotinaldehyde benzoyl hydrazone (HBH), or salicylaldehyde benzoyl hydrazone (SBH).

Concentration Dependence of Collagen Suppressing Effects of Pyridoxal Benzoyl Hydrazone and Aldehyde Analogs Thereof FIG. 3 illustrates collagen synthesis in fibroblast cultures treated for 72 hours with various concentrations of PBH, 3-hydroxyisonicotinaldehyde benzoyl hydrazone (HBH), or salicylaldehyde benzoyl hydrazone (SBH), as measured by collagenase digestion of proteins labeled with [2,3-$^3$H] proline. The PBH curve is derived from FIG. 2.

EXAMPLE 4

Antiproliferative Effect of Pyridoxal Benzoyl Hydrazone

Figure 4:
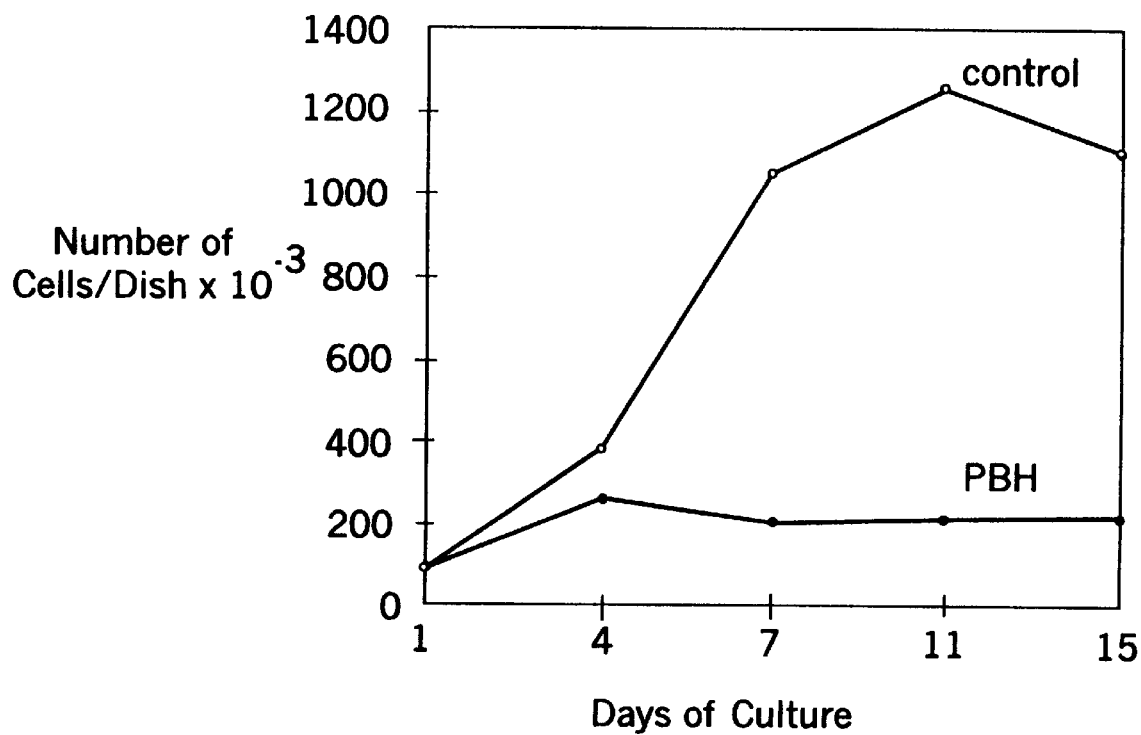
FIG. 4 illustrates fibroblast cultures treated on day 1 with 15 uM of PBH, which were then allowed to proliferate for various lengths of time.

FIG. 4 illustrates fibroblast cultures treated on day 1 with 15 uM of PBH, which were then allowed to proliferate for various lengths of time. The number of cells recovered was determined electronically.

EXAMPLE 5

Figure 5:
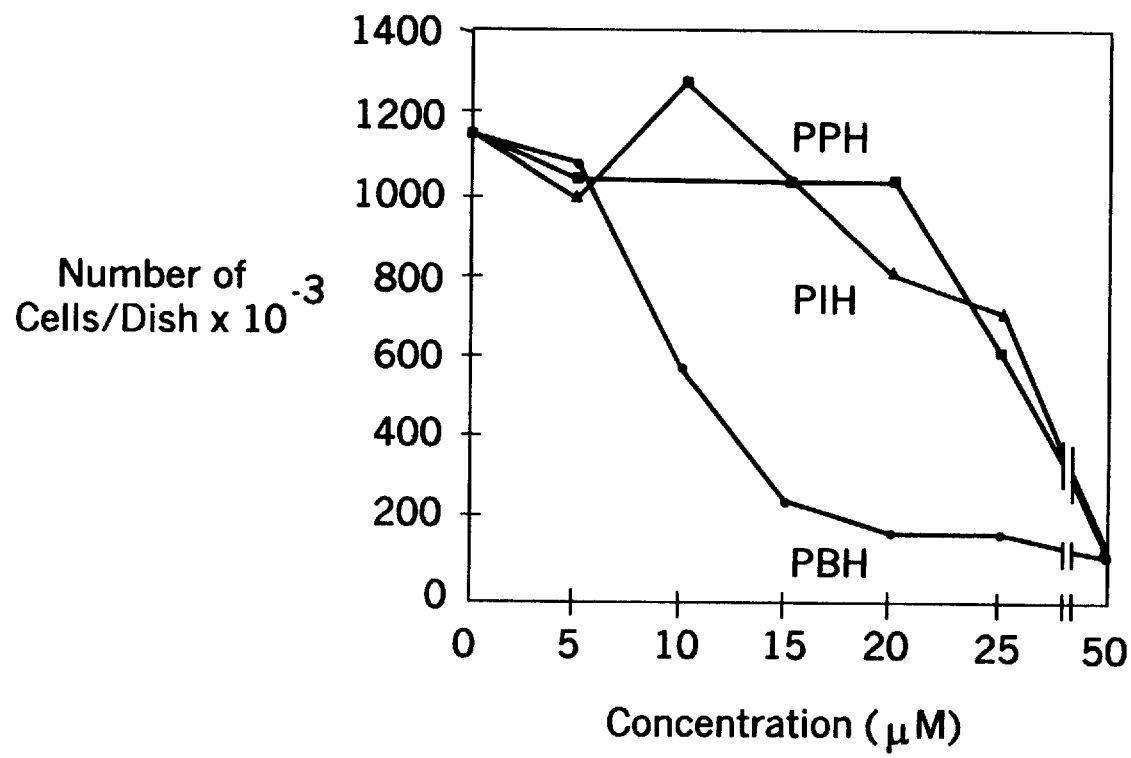
FIG. 5 illustrates fibroblast cultures treated with various concentrations of PBH, PIH, or PPH, which were allowed to proliferate for seven days.

Concentration Dependence of Anti-proliferative Effects of Pyridoxal Benzoyl Hydrazone and Acyl Analogs Thereof FIG. 5 illustrates Fibroblast cultures treated with various concentrations of PBH, PIH, or PPH, which were allowed to proliferate for seven days. The number of cells recovered was determined electronically.

EXAMPLE 6

Figure 6:
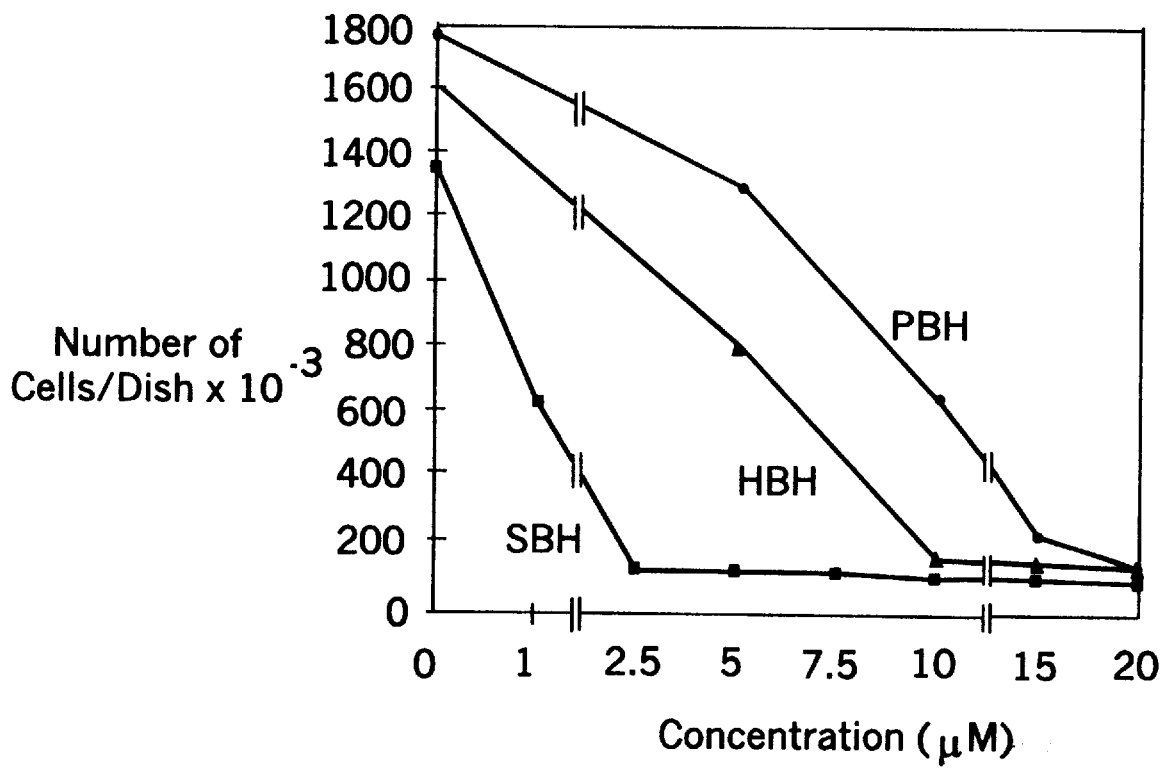
FIG. 6 illustrates fibroblast cultures treated with various concentrations of PBH, HBH, or SBH, which were allowed to proliferate for 7 days.

Concentration Dependence of Anti-proliferative Effects of Pyridoxal Benzoyl Hydrazone and Aldehyde Analogs Thereof FIG. 6 illustrates fibroblast cultures treated with various concentrations of PBH, HBH, or SBH, which were allowed to proliferate for 7 days. The number of cells recovered was determined electronically.

EXAMPLE 7

Effect of Pyridoxal Benzoyl Hydrazone on Cell Viability

The effect of pyridoxal benzoyl hydrazone on cell viability is given in Table 1 below, which shows the viability of fibroblasts recovered after six days of treatment with 15 $\mu$M pyridoxal benzoyl hydrazone under proliferating conditions, as determined by trypan-blue dye exclusion. The values represent the mean ±SD for three cultures.

TABLE 1

| Treatment | Viability (%) |
| --- | --- |
| Control | 95 ± 1 |
| PBH | 94 ± 1 |

The foregoing examples are illustrative of the present invention, and are not to be construed as limiting thereof. The invention is defined by the following claims, with equivalents of the claims to be included therein.

That which is claimed is:

1. A method of inhibiting fibrosis in a subject afflicted with a fibrosing disorder, comprising administering to said subject an effective fibrosis-inhibiting amount of a compound of Formula (I):

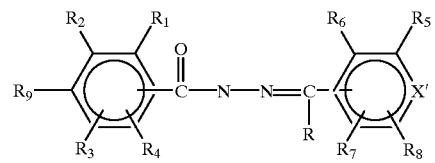

wherein:

X' is selected from the group consisting of N and CR$_9$;

R is selected from the group consisting of H and loweralkyl;

R$_1$, R$_2$, R$_3$, R$_4$, R$_5$, R$_6$, R$_7$, and R$_8$ are each independently selected from the group consisting of H, loweralkyl, hydroxy, loweralkylhydroxy, amino, and nitro;

R$_9$ is H or loweralkyl;

or a pharmaceutically acceptable salt thereof.

2. A method according to claim 1, wherein R is H.

3. A method according to claim 1, wherein X' is CH and R$_1$, R$_2$, R$_3$ and R$_4$ are H.

4. A method according to claim 1, wherein said compound is selected from the group consisting of pyridoxal benzoyl hydrazone, 3-hydroxyisonicotinaldehyde benzoyl hydrazone, salicylaldehyde benzoyl hydrazone, and the pharmaceutically acceptable salts thereof.

5. A method according to claim 1, wherein said subject is afflicted with a dermal fibrosing disorder.

6. A method according to claim 1, wherein said subject is afflicted with fibrosis of an internal organ.

7. A method according to claim 1, wherein said subject is afflicted with a fibrotic condition of the eye.

8. A method according to claim 1, wherein said compound is administered topically.

9. A method according to claim 1, wherein said compound is administered parenterally.

* * * * *

UNITED STATES PATENT AND TRADEMARK OFFICE
CERTIFICATE OF CORRECTION

PATENT NO. : 6,005,009
DATED : December 21, 1999
INVENTOR(S) : Murad et al.

It is certified that error appears in the above-identified patent and that said Letters Patent is hereby corrected as shown below:

In the Abstract

[57], line 1, delete "comprising" and insert - - comprise --.
[57], line 2, after "thereof" delete "are disclosed" and insert - - . - -.
[57], line 4, after "hydrazone" insert - - pyridoxal isonicotinoyl hydrazone, pyridoxal phenylacetyl hydrazone - -.

In the Claims

Claim 3, column 6, line 43, delete "X'" and insert - - X - -.
Claim 9, column 6, line 62, delete "parenterally" and insert - - pareneterally - -.

Signed and Sealed this

Twenty-ninth Day of May, 2001

*Attest:*

NICHOLAS P. GODICI

*Attesting Officer*      *Acting Director of the United States Patent and Trademark Office*